United States Patent [19]

Kohne et al.

[11] Patent Number: 5,132,207

[45] Date of Patent: Jul. 21, 1992

[54] ACCELERATED NUCLEIC ACID REASSOCIATION METHOD

[75] Inventors: David E. Kohne, La Jolla; Daniel L. Kacian, San Diego, both of Calif.

[73] Assignee: Gen-Probe Incorporated, San Diego, Calif.

[21] Appl. No.: 644,879

[22] Filed: Jan. 23, 1991

Related U.S. Application Data

[63] Continuation of Ser. No. 816,711, Jan. 7, 1986, abandoned, which is a continuation-in-part of Ser. No. 627,795, Jul. 5, 1984, abandoned.

[51] Int. Cl.$^5$ .................... C12Q 1/68; C07H 15/12; C07H 17/00
[52] U.S. Cl. ............................ 435/6; 536/27; 935/1; 935/78; 935/80
[58] Field of Search ............... 435/6; 536/27; 935/1, 935/78, 80

[56] References Cited

U.S. PATENT DOCUMENTS

4,302,204 11/1981 Wahl et al. ............................ 435/6

FOREIGN PATENT DOCUMENTS

0127327 5/1984 European Pat. Off. .

OTHER PUBLICATIONS

Hames et al Nucleic Acid Hybridization (1985); IRL Press Wash D.C.
Britten et al, "Analysis of Repeating DNA Sequence by Reassociation" in Methods in Enzymology 29, 363–418 (1974).
Angerer et al, Chromosoma (Berl) vol. 56, pp. 213–226 (1976).
Casey et al, Nucleic Acids Research, vol. 4, pp. 1539–1552 (1977).
Van Ness et al."Physical Parameters Affecting the Rate and Completion of RNA Driven Hybridization of DNA: New Measurements Relevant to Quantitation Based on Kinetics", Nucleic Acids Research, vol. 10, p. 8061–8077 (1982).
Orosz et al, Biopolymers, vol. 14, pp. 2517–2524 (1975).
Wetmur et al, "Kinetics of Renaturation of DNA", J. Mol. Biol. 31, 349–370 (1968).
Wetmur, "Acceleration of DNA Renaturation Rates", Biopolymers, 14, 2517–2524 (1975).
Chiang-Tung, et al., "Effects of Microscopic and Macroscopic Viscosity on the Rate of Renaturation of DNA", Biopolymers, vol. 13, 1974, pp. 1847–1858.
Cox, et al., "Renaturation of DNA: A Novel Reaction of Histones", Nucleic Acids Research, vol. 9, 1981, pp. 389–400.
Galau, et al., "Studies on Nucleic Acid Reassociation Kinetics: Retarded Rate of Hybridization of RNA with Excess DNA", Proc. Natl. Acad. Sci. USA, vol. 74, 1977, pp. 2306–2310.
Kohne, et al., "Room Temperature Method for Increasing the Rate of DNA Reassociation by Many Thousandfold: The Phenol Emulsion Reassociation Technique", Biochemistry, vol. 16, 1977, pp. 5329–5341.
Lamar, et al., "Y-Encoded, Species-Specific DNA in Mice: Evidence that the Y Chromosome Exists in Two Polymorphic Forms in Inbred Strains", Cell, vol. 37, 1984, pp. 171–177.
Murray, et al., "Ancient Repeated Sequences in the Pea and Mung Bean Genomers and Implications for Genome Evolution", J. Mol. Evol. (in press).
Orosz, et al., "DNA Melting Temperatures and Renaturation Rates in Concentrated Alkylammonium Salt Solutions", Biopolymers, vol. 16, 1977, pp. 1183–1199.
Renz, et al., "A Colorimetric Method for DNA Hybridization", Nucleic Acids Research, vol. 12, 1984, pp. 3435–3444.
Wahl, et al., "Efficient Transfer of Large DNA Fragments from Agarose Gels to Diazobenzyloxymethyl-Paper and Rapid Hybridization by Using Dextran Sulfate", Proc. Natl. Acad. Sci. USA., vol. 76, 1979, pp. 3683–3687.
Lederman et al Anal Biochem 117 (1981) pp. 158–163.
Orosz DNA Iodination, Provirus Isolation, Excluded Volume and Electrostatic Effects on DNA Renaturation Rate; PhD thesis 1975 Indexed on Chemical Abstracts; obtained from Xerox University Microfilms, Ann Arbor, Mich. pp. 167–181.

*Primary Examiner*—Margaret Moskowitz
*Assistant Examiner*—Scott A. Chambers
*Attorney, Agent, or Firm*—Lyon & Lyon

[57] ABSTRACT

A method for the formation of double stranded nucleic acid molecules from separate single stranded nucleic acid molecules in a single phase reaction solution is disclosed wherein the rate of reaction is greatly increased over the rate of reaction at standard reference conditions. The greatly accelerated reaction rate is accomplished through the use of known concentrations of nucleic acid precipitating agents which are added to the reaction solution. Nucleic acid denaturing agents may also be added. The solution so formed is incubated and then assayed for the presence of double stranded nucleic acid molecules.

44 Claims, No Drawings

ACCELERATED NUCLEIC ACID REASSOCIATION METHOD

This Application is a file wrapper continuation of U.S. Ser. No. 6/816,711, filed Jan. 7, 1986, now abandoned, which is a continuation-in-part of pending application Ser. No. 627,795, filed Jul. 5, 1984, now abandoned.

BACKGROUND OF THE INVENTION

1. Field of The Invention

The present invention is directed to a method for the renaturation, reassociation or hybridization of single stranded nucleic acid molecules into double stranded nucleic acid molecules wherein the rate of reaction is greatly increased over the rate of reaction under standard reference conditions of 0.12M phosphate buffer at 60° C. More particularly, the present invention is directed to a method for the renaturation, reassociation or hybridization of nucleic acids, including DNA to DNA, RNA to DNA, and RNA to RNA reactions wherein the rate of the reaction is greatly increased by factors of 50 to 100 times, and even up to several thousand times that of the reaction rates observed under standard reference conditions. These greatly accelerated reaction rates are achieved through the utilization of reaction solutions containing nucleic acid precipitating agents.

2. Description of The Prior Art

Numerous methods for the nucleation of single stranded nucleic acid molecules into double stranded molecules are known in the art and have proven to be useful tools for the analysis of genetic material from a wide variety of organisms. Generally speaking, these nucleation reactions, renaturation, reassociation and hybridization, are based on the tendency of single stranded nucleic acid molecules having blocks or segments of complementary base sequences to form base paired structures between these complementary sequences and to rewind forming double helices. The greater the extent of sequence complementarity between the single stranded nucleic acid molecules, the greater the tendency for a given pair of molecules to nucleate and form a double stranded or duplex molecule.

Renaturation, reassociation and hybridization are essentially synonymous reactions between single stranded nucleic acid molecules. As such, they will be discussed interchangeably throughout the body of this paper. However, the following distinction may prove helpful in understanding the technology involved. Renaturation generally refers to the formation of a double stranded nucleic acid molecule from two single stranded molecules which were originally base paired to one another and separated through a denaturation process. Reassociation refers to the process of forming double stranded nucleic acid molecules between two single stranded molecules which usually come from different original molecules. Hybridization refers to the formation of double stranded nucleic acid molecules from single stranded nucleic acid molecules of individual origin with respect to one another. It should be appreciated that these are not clear cut distinctions and that there is considerable overlap between them. For example, DNA:DNA reactions are commonly called both reassociation and hybridization reactions. On the other hand, the formation of an RNA:RNA double stranded molecule is generally referred to as hybridization.

The kinetics of these reactions are well understood in the art also following second-order kinetics. Thus, as the concentration of the single stranded nucleic acid molecules is increased, the rate of the reaction is also increased. Conversely, decreasing the concentration of the single stranded nucleic acid reactant will decrease the rate of reaction and thus increase the time necessary for the formation of the double stranded nucleic acid molecules to take place.

The effect of temperature on the reaction rate is also well known in the art. As the temperature of the reaction decreases below the $T_m$ (the temperature at which 50% of the double stranded molecules is denatured, also known as the "melting temperature") a maximum rate for the reaction is achieved at temperatures of approximately 15° C. to 30° C. below the $T_m$. Further decreases in temperature are known to decrease the rate below this maximum rate.

Lastly, with respect to the kinetics of these reactions, it is known that the reaction rates are very dependent on the ionic strength below 0.4M for electrolytes such as NaCl and are almost independent of the salt concentration above this ionic strength.

More information on the kinetics and reaction rates of these nucleic acid association reactions can be found in the following publications:

Wetmur, R., and Davidson, N. (1968), *J. Molec. Biol.* 31, 349;

Wetmur, R. (1975), *Biopolymers* 14, 2517;

Britten, R., J., Graham, D., and Neufeld, B. (1974), *Methods Enzymol,* 29, 363;

Kohne, D. E., Levinson, S. A., and Byers, M. J. (1977) *Biochemistry* 16, 5329; and Orosz, J. M., and Wetmur, J. G., (1977) *Biopolymer* 16, 1183.

It has long been recognized in the art that a major limitation on the utility of these known nucleic acid association techniques is the basic rate of the reaction. Reaction times on the order of several hours to tens of hours and even days are commonplace. Increasing the reaction rate by increasing the quantities of single stranded nucleic acid molecules utilized in the reactions (due to the second-order kinetics) is not a desirable solution to this problem for three reasons. First, in many cases the target single stranded nucleic acid in the reaction is extracted from physiological samples which inherently limits the amount of such nucleic acid available to that contained in the cells of the physiological sample. Secondly, there are significant expenses associated with the use of nucleic acid reactants which limits the practical utility of increasing the quality of reactants. Thirdly, increasing the quantities of single stranded nucleic acid molecules decreases the sensitivity of the reaction by increasing the background noise. Nonetheless, a number of techniques have been developed to increase the basic rate of these reactions by factors of 5 to 50 or more. Techniques of limited applicability have also been developed which increase the basic reaction rate by factors on the order of 1000 or more. However, as will be discussed in detail below, none of these prior art techniques has been successful at producing greatly accelerated reaction rates of 50 to 100 times or more than the basic reference standard reaction in a single phase system applicable to DNA:DNA, DNA:RNA, and RNA:RNA reactions.

When dealing with reaction rates, the accepted standard reference condition for the comparison of these rates is an aqueous solution of 0.12M phosphate buffer (PB) at 60° C. A similar standard reference condition that is often used giving comparable reaction rates is an aqueous solution of 0.18M NaCl at 60° C.

By far the most common technique of accelerating the reaction rate above that of the standard reference condition has been to increase the salt concentration of the reaction solution above that of the standard reference condition. As detailed in following table, while significant reaction rate increases are observed by increasing the salt concentration, the prior art techniques indicate that the rate of increase levels off or even falls for salt concentrations above 2M.

TABLE 1

PRIOR ART KNOWLEDGE OF EFFECT OF SALT CONCENTRATION ON DNA:DNA HYBRIDIZATION RATES

| Salt | Rate increase relative to 0.18M NaCl reference condition | |
|---|---|---|
| A. Sodium Chloride | | |
| 0.18M | 1 | |
| 0.72M | 5.8 | |
| 1M | 7 | |
| 1.2M | 7.7 | Britten, et al. |
| 1.85M | 8.6 | |
| 3.2M | 12.3 | |
| 4.75M | 21 | |
| B. Cesium Chloride | | |
| 1M | 7.6 | |
| 4M | 12.7 | |
| 7.5M | 15.6 | |
| C. Sodium Phosphate | | |
| 0.12 (0.18M Na) | 1 | |
| 0.48M (0.72M Na) | 5.6 | Britten, et al. and |
| 1M (1.5M Na) | 8.4 | Wetmur and Davidson |
| 1.23M (1.85M Na) | 10.1 | |
| 2.1 (3.2M Na) | 12.1 | |
| D. Sodium Perchlorate | | |
| 1M | 11 | |
| 2.2M | 6.8 | Wetmur and Davidson |
| 4.0M | 3.4 | |
| 5.2M | 1.5 | |
| 6.4M | 0.7 | |
| E. Lithium Chloride | | |
| 0.4M | 3.9 | Orosz and Wetmur |
| 1M | 11.6 | |
| F. Potassium Chloride | | |
| 0.7M | 5.3 | |
| 1M | 5.8 | |
| 2M | 5.4 | Orosz and Wetmur |
| 3M | 10.0 | |
| 4M | 11 | |
| G. Sodium Bromide | | |
| 3M | 9 | Orosz and Wetmur |
| H. Sodium Sulfate | | |
| 3M | 9 | Orosz and Wetmur |
| I. Ammonium Chloride | | |
| 4M | 30 | |

While the data in Table 1 relates to the rate increases found with respect to DNA:DNA reactions, it will be appreciated that the reaction rates of RNA with DNA are reported as being less affected by changes in salt concentration. Other researchers have demonstrated that for salt concentrations above the standard reference conditions, the relative rate of RNA:DNA reaction is affected to about one-half the extent of those rates found for DNA:DNA reactions when the RNA used has comparatively little secondary structure. For RNA reactants with more secondary structure, the effect of elevated salt concentration has been found to be even less. In fact, no change in rate is observed for hybridization of excess RNA with DNA over comparative ranges of salt concentrations (see, e.g., Van Ness, J. and Hahn, W. E. (1982) Nucl. Acids. Res. 10, 8061).

While little data is available for RNA:DNA hybridization where the DNA is the excess reactant, it is commonly assumed in the art that the effect of elevated salt concentration on such a reaction system is comparable to that of the excess RNA system.

An alternative approach to the acceleration of the rate of these nucleic acid association reactions is the previously developed two-phase phenol aqueous emulsion technique for the reassociation of DNA to DNA (Kohne, D. E., Levinson, S. A., and Byers, M. J. (1977) Biochemistry 16, 5329). In this two-phase system, the agitation of an emulsion formed between phenol and an aqueous salt solution has produced greatly accelerated reaction rates over 100 times faster than comparative standard condition rates. However, the two-phase phenol emulsion technique has not produced similarly greatly accelerated reaction rates for RNA:RNA and RNA:DNA systems. The greatest reaction rate increase observed for RNA:RNA and RNA:DNA reactions is only 50 to 100 times that of the standard reference condition rate. This technique is further limited in that reaction will not occur unless an emulsion is present and agitated and the reaction temperature is below 75° C.

A number of other techniques for producing reaction rate increases on the order of 10 fold above the standard reference condition rate have utilized the volume exclusion principle to promote the acceleration of the reaction rate. These techniques utilize the synthetic polymers polyethylene glycol, dextran, or dextran sulfate to reduce the volume of reaction solution available to the nucleic acid reactants and thereby increase their effective concentration. However, while reaction rate increases of 10 to 15 fold over the standard reference condition rate for DNA:DNA reactions have been reported, rate increases of only about 3 fold are reported for RNA:DNA reactions. Details of these techniques can be found in the following publications:

Renz, M., and Kurz, C. (1984) Nucl. Acids Res. 12, 3435; and

Wahl, G. M., Stern, M., and Stark, G. R. (1979) Proc. Natl. Acad. Sci. USA 75, 3683.

Accordingly, it is a principal object of the present invention to provide a method for the renaturation, reassociation, or hybridization of nucleic acids that produces a greatly accelerated reaction rate on the order of 100 or more times that of the standard reference condition rate and that is applicable to DNA:DNA, RNA:DNA, or RNA:RNA reaction systems. Additionally, it is a further object of the present invention to provide a method that promotes greatly accelerated reaction rates without requiring the utilization of a two-phase system or the formation of an emulsion. It is a further object of the present invention to provide a method wherein greatly accelerated reaction rates are obtainable without the need to increase the concentrations of single stranded nucleic acid reactants. Lastly, it is an additional object of the present invention to provide a method for greatly accelerating the rate of these nucleic acid association reactions that is widely applicable to a variety of reaction mixture volumes and hybridization temperatures.

SUMMARY OF THE INVENTION

Generally stated, the present invention accomplishes the above described objectives by providing a method for the formation of double stranded nucleic acid molecules from separate single stranded nucleic acid molecules wherein a single phase reaction solution incorporating a known concentration of at least one nucleic acid precipitating agent is utilized to greatly increase the reaction rate over the standard reference condition reaction rate. By 'standard reference condition reaction rate', is meant the reaction rate in an aqueous solution of 0.18M NaCl at 60° C., unless the contrary is indicated. However as already pointed out, a comparable reaction rate is obtained using the conditions of 0.12M phosphate buffer at 60° C. By 'greatly increase' (or its equivalent term, 'greatly accelerate') the reaction rate in the foregoing context, is meant a rate increase of at least about 100 times over the standard reference condition reaction rate. The improved method of the present invention is widely applicable to a broad range of reaction solution volumes and nucleic acid concentrations and promotes reaction rates on the order of 100 to 1000 fold greater than the standard reference condition reaction rate for DNA:DNA, RNA:DNA and RNA:RNA reactions.

More particularly, the method of the present invention comprises the steps of preparing an aqueous reaction solution containing complementary single stranded nucleic acids, one of which preferably incorporates a detectable marker, and a known concentration of at least one nucleic acid precipitating agent. The aqueous reaction solution so prepared is incubated at a temperature at which hybridization can occur and then assayed for the presence of double stranded nucleic acid molecules.

Additionally, alternative methods of the present invention are disclosed wherein the aqueous reaction solution also contains a known concentration of a nucleic acid denaturing agent and also where the nucleic acid precipitating agent is contained in a second solution which is added to the aqueous reaction solution before the incubation step.

The nucleic acid precipitating agents which are utilized to practice the various alternative methods of the present invention are preferably selected from the group consisting of detergent, dihydroxybenzene, sodium dodecyl sulfate, sodium diisobutyl sulfosuccinate, sodium tetradecyl sulfate, Sarkosyl, and the alkali metal salts and ammonium salts of $SO_4$, $PO_4$, Cl, and HCOO. The salt concentrations preferably range from about 1M to about 10M. Additionally, it is preferred that the aqueous reaction solutions are prepared to have a pH ranging from about 4 to 11 and the concentration of the organic compound strong nucleic acid precipitating agents preferably ranges from approximately 5 volume % to 95 volume % and the preferred concentration of the nucleic acid denaturing agents ranges from approximately 5 volume % to 95 volume %.

Incubation temperatures preferably range from just below the $T_m$ of the double stranded nucleic acid association product to temperatures approaching room temperature of approximately 22° C. It will be appreciated that the addition of nucleic acid denaturing agents to the aqueous reaction solution will lower the temperature at which hybridization occurs. The hybridization temperatures for most reactions utilizing the methods of the present invention will range from approximately room temperature to 90° C.

After incubation, the reaction solution is assayed through a variety of known assay techniques to detect the presence of the double-stranded nucleic acid product. A preferred assay procedure utilizes hydroxyapatite (HA) for this purpose.

Further objects, features and advantages of the method of the present invention will become apparent to those skilled in the art from a consideration of the following detailed description. The following abbreviations are offered as an aid to understanding the specification.

ABBREVIATIONS

PB: Sodium phosphate solution. (A mixture of equimolar amounts of $Na_2HPO_4$ and $NaH_2PO_4$.)
PK: Proteinase K
EGTA: Ethylene glycol bis-$\beta$-aminoethyl ether) N,N,N',N'-tetraacetic acid
HA: Hydroxyapatite
STDS: Sodium tetradecyl sulfate
SDIBSS: Sodium diisobutyl sulfosuccinate
Tris: Tris(hydroxymethyl)aminomethane hydrochloride
G HCl: Guanidine hydrochloride
DNA: Deoxyribonucleic acid
RNA: Ribonucleic acid
rRNA: Ribosomal ribonucleic acid
cDNA: Complementary DNA
DTT: Dithiothreotol
SDS: Sodium dodecyl sulfate

DETAILED DESCRIPTION OF THE INVENTION

In a broad aspect, the method of the present invention is based upon the surprising discovery that relatively high concentrations of nucleic acid precipitating agents (both salts and organic compounds) will greatly accelerate the rate at which single stranded nucleic acid molecules with regions of complementary base sequences will combine to form base paired double stranded nucleic acid molecules. Reaction rates are increased as much as 800 times over the standard references condition rate for DNA:DNA reactions and as much as 3000 times over the standard reference condition rate for RNA:DNA reactions and as much as 1000 times over the standard reference condition rate for RNA:RNA reactions. What is more, these greatly increased reaction rates occur in a one-phase system and no emulsion or shaking is required.

Such significant increases in the rate of these reactions comes in complete contrast to the teaching of the prior art. For example, an often used accelerated reaction condition is approximately 1M NaCl (or an equivalent to it) which produces a reaction rate approximately 8 to 25 times faster than the reference standard condition. Such a rate increase is not the "greatly accelerated" rate disclosed by the present invention. As shown by the prior art table discussed above, increasing the concentration of NaCl to 4.75M results in little more of a rate increase. Similarly, concentrations of CsCl (also commonly used to promote increased reaction rates) up to 7.5M produce analogous increases of approximately 15 times that of the standard reference condition rate. Similar rate increases over the standard reference condition rate were also found for 1M $(NH_4)_2SO_4$ and 1M LiCl, each salt producing rate increases of approximately 13 fold to 18 fold, which is roughly comparable to the rate increase observed for 1M NaCl or CsCl. However, in contrast to these known results, it was surprisingly discovered that increasing the concentration of $(NH_4)_2SO_4$ to 2M greatly increased the reaction rate by an additional factor of 33 to approximately 600 times that of the standard reference condition rate. Additional research disclosed a comparable rate increase when the concentration of LiCl was increased to 4M wherein a rate increase of an additional 30 fold was observed, producing an accelerated reaction rate 467 times greater than that of the standard reference condition. Comparable patterns of great acceleration were also discovered for ammonium formate, cesium sulfate, sodium sulfate, lithium sulfate, sodium phosphate and several detergents and organic compounds.

These same factors (aggregation or precipitation) which prevented the earlier researchers from discovering the method of the present invention are also proposed as being responsible for the greatly accelerated reaction rates of the methods of the present invention. It is hypothesized that nucleic acid precipitating agents cause the single stranded nucleic acid molecules to aggregate and thereby stimulate the reaction rate. As discussed above, the rate at which a given pair of complementary single stranded nucleic acids will form double stranded nucleic acid molecules is directly related to their concentration in the reaction solution. The higher the nucleic acid concentration, the faster the rate of reaction. In the presence of a nucleic acid precipitating agent, the single stranded nucleic acid molecules aggregate or associate together in solution. This aggregation or semi-precipitation results in high concentrations of nucleic acid in localized regions of the reaction solution. If the aggregation occurs at a temperature where hybridization or reassociation can occur, the rate of the reaction is greatly increased.

In order for the complementary single stranded nucleic acid molecules to reassociate or hybridize together in a reaction solution containing a nucleic acid precipitating agent, the temperature must be high enough for the reaction to occur. Renaturation, reassociation or hybridization usually occurs at optimal rates at roughly 10° C. to 30° C. below the $T_m$ of the double stranded nucleic acid molecule involved. In the reaction solution of the present invention, the $T_m$ of most double stranded nucleic acid molecules will range from 85° C. to 100° C. When the reaction solution of the present invention contains one or more nucleic acid denaturing agents, the $T_m$ will be greatly lowered and temperatures as low as room temperature can be utilized to achieve optimum reaction rates. Accordingly, reaction temperatures of approximately 20° C. to 90° C. should produce optimum rates of reaction.

As discussed above, a variety of nucleic acid precipitating inorganic salts have been discovered to greatly increase the rate of reaction when used at sufficiently high concentrations. In general, the salts which have been effective for the method of the present invention are those which contain at least one of the stronger salting out cation or anion groups (namely $SO_4$, $PO_4$, Li, $NH_4$). Additionally, organic compounds which are miscible with the reaction solution and which have precipitating or salting out properties are also effective in promoting greatly accelerated reaction rates. Examples of such compounds include detergent, dihydroxybenzene, Sarkosyl, sodium dodecyl sulfate, sodium diisobutyl sulfosuccinate and sodium tetradecyl sulfate.

To determine which salts or other compounds possess the requisite nucleic acid precipitating properties to practice the method of the present invention, it is necessary to first screen the compounds to determine if the compounds will precipitate single stranded nucleic acid molecules and then to determine whether the precipitate so formed will disappear when the reaction solution is heated to a temperature where reaction can occur. The nucleic acid precipitating agents are then analyzed to determine the preferred concentrations and incubation temperatures for producing optimal reaction rate increases. This screening procedure also makes it possible to determine the effective concentration of the nucleic acid precipitating agent necessary to promote greatly increased reaction rates.

For example, Sarkosyl (N-lauroylsarcosine sodium salt) was screened for its ability to increase nucleic acid reassociation rates in the following manner. First, a series of solutions containing known amounts of purified liver RNA (final concentration at 4 mg/ml) and varying amounts of Sarkosyl (ranging from approximately 9 volume % to 24 volume %) were prepared. The solutions were thoroughly mixed and checked for the presence of a precipitate using either direct visual observation or a spectrophotometer using a wavelength at which neither the Sarkosyl or the nucleic acid absorbs. If a precipitate was observed in a solution, the solution was heated to approximately 40° C. to 90° C. to determine whether the degree of precipitation would change. It was found that at 10% to 14% Sarkosyl, little or no precipitation of the nucleic acid was observed. However, at higher concentrations, Sarkosyl was found to precipitate nucleic acid. A number of further experiments were then conducted to determine the preferred concentration and incubation temperatures for producing optimal reaction rate increases.

The following tables are an illustrative listing of the reaction rate increases that can be expected with a variety of concentrations of preferred inorganic salt nucleic acid precipitating agents.

TABLE 2

THE EFFECT OF HIGH CONCENTRATIONS OF CERTAIN SALTS ON DNA:DNA HYBRIDIZATION RATE

| Salt | Rate increase relative to 0.18M Na reference condition |
|---|---|
| A. Ammonium Sulfate | |
| 1M | 17.5 |
| 2M | 600 |
| 2.1M | 600 |
| 2.5M | 467 |
| 3.1M | 70 |
| B. Lithium Chloride | |
| 1M | 13 |
| 3.5M | 66 |
| 4M | 467 |
| 5M | 280 |
| 6M | 19 |
| C. Other Salts | |
| 2M Cesium Sulfate | 280 |
| 1.9M Sodium Sulfate | 600 |
| 2M Lithium Sulfate | 420 |
| 6M Ammonium Formate | 210 |
| 2.4M Sodium Phosphate | 800 |

TABLE 3

EFFECT OF HIGH CONCENTRATIONS OF SALTS ON EXCESS RNA:DNA HYBRIDIZATION RATES

| Salt | Rate increase relative to reference 0.18M Na condition |
|---|---|
| 0.18M Sodium Chloride | 1 |
| 0.72M Sodium Chlroide | 3.6 |
| 2M Ammonium Sulfate | 1500 |
| 2.4M Sodium Phosphate | 3000 |
| 4M Lithium Chloride | 600 |
| 2M Sodium Sulfate | 3460 |
| Ammonium Sulfate | |
| 1M | 90 |

TABLE 3-continued
EFFECT OF HIGH CONCENTRATIONS OF SALTS ON EXCESS RNA:DNA HYBRIDIZATION RATES

| Salt | Rate increase relative to reference 0.18M Na condition |
|---|---|
| 2M | 1500 |
| 3M | 600 |

With this understanding of the nucleic acid precipitating agents, the method of the present invention is as follows. The first step of the preferred method is the preparation of an aqueous reaction solution containing a quantity of a first single stranded nucleic acid molecule and a quantity of a second single stranded nucleic acid molecule, preferably incorporating a detectable marker and at least one segment of base sequences which are complementary to a corresponding segment of base sequences of the first single stranded nucleic acid molecule. Additionally, a known concentration of at least one of the previously discussed nucleic acid precipitating agents is also incorporated into the aqueous reaction solution in a concentration sufficient to greatly accelerate the rate of reaction by a factor of at least 50 to 100 times the rate of the standard reference condition reaction. Outside of practical consideration such as the solubility limit of the single stranded nucleic acid reactants, there is no real limit as to the volume of aqueous reaction solution that may be utilized to practice the method of the present invention or to the quantity of single strand nucleic acid molecule reactants as well. Additionally, while it should be emphasized that the nucleic acid precipitating agent is all that is necessary to obtain the greatly increased reaction rates, additional additives may be incorporated into the aqueous reaction solution such as buffers, EGTA, EDTA, SDS, SK, PK, ETOH, Urea, Guanidine HCL, Glycogen and dilute Amphyl. Additionally, it should be noted that while it is preferred that at least one of the single stranded nucleic acid molecule reactants incorporates a detectable marker, the marker is not essential to promoting the greatly accelerated reaction rates.

The next step of the method of the present invention is to incubate the aqueous reaction solution. As discussed above, temperatures ranging from just below the $T_m$ to approximately room temperature are sufficient for incubating the reaction solution. The actual temperature utilized will vary depending on the concentrations of the reactants and whatever additional additives are incorporated into the reaction solution. However, most reactions will be conducted at incubation temperatures ranging from approximately room temperature to 90° C.

The last step in the method of the present invention is to assay the incubated aqueous reaction solution for the presence of double stranded nucleic acid molecules. A wide variety of assaying techniques are known in the art and are contemplated as being within the scope of the present invention. A preferred assaying technique involves the removal of an aliquot from the incubated reaction solution at a specified time after the start of the reaction. The aliquot is diluted into 1 ml of 0.14M PB, 0.02% sodium dodecyl sulfate (SDS). The diluted solution is then passed over a column of hydroxyapatite (HA) (bed volume equaling 1 ml) which has been preequilibrated to 0.14M PB, 0.02% SDS at 67° C. Single stranded DNA molecules will not bind to the HA, but RNA and double stranded nucleic acid molecules will be adsorbed to the column. Nonhybridized single stranded nucleic acid molecule are then removed from the column by passing 5 ml of column buffer 0.14M PB, 0.02% SDS over the column. The adsorbed nucleic acid is recovered from the column by eluting the column with 0.3M PB at 67° C. The various solution fractions so produced may then be assayed for the detectable marker (such as radioactive hydrogen or iodine).

An alternative preferred method of assaying the incubated aqueous reaction solution for the presence of double strand nucleic acid follows.

(a) Remove an aliquot from the solution to tested and mix with 5 ml of 0.14M PB, 0.02% SDS containing one 0.1 gm of HA. Vortex the mixture for 5-10 seconds.

(b) Incubate the mixture at 72° C. for 5 minutes.

(c) Centrifuge the mixture in a table top centrifuge for 1 minute to pellet the HA. Discard the supernate fraction.

(d) Add 5 ml of 0.14M PB, 0.02% SDS to the tube and vortex to resuspend the HA.

(e) Repeat (c).

(f) Assay the HA for detectable marker.

An alternative approach for practicing the method of the present invention incorporates the additional step of mixing a second solution containing the nucleic acid precipitating agent into the previously prepared aqueous reaction solution prior to incubating the resultant mixture. Thus, the alternative method comprises the steps of preparing the previously discussed aqueous reaction solution, mixing the aqueous reaction solution with a second solution containing a known concentration of at least one nucleic acid precipitating agent which is miscible with the aqueous solution and capable of precipitating single stranded nucleic acid molecules from an aqueous solution, incubating the resulting mixture at the previously discussed temperatures, and assaying the incubated mixture for the presence of double stranded nucleic acid molecules. This alternative method serves to eliminate any problems which may occur with the premature aggregation of the single stranded nucleic acid molecule reactants in the aqueous reaction solution.

An additional modification to both of the alternative methods for practicing the accelerated rate reaction of the present invention involves the addition of a known concentration of at least one nucleic acid denaturing agent such as alcohol to the aqueous reaction solution. Preferably the concentration of denaturing agent added will range from approximately 5% by volume to approximately 95% by volume. For example, alcohol is a denaturant and functions to lower the temperature at which the reaction will occur. Ethanol is soluble in 2M $(NH_4)_2SO_4$ to approximately 20%. At this concentration, the reaction will occur at a temperature of approximately 49° C. instead of the usual 60° C. to 80° C.

Another denaturing agent which can be added to the aqueous reaction mixture is Urea. The presence of Urea in the reaction mix has little effect on the extent or rate of hybridization in several of the accelerated rate systems checked thus far. Example 36 is an example of one such system. Urea is an excellent solubilizing agent for many non-nucleic acid compounds which may be present in a sample and is useful to minimize any effect these compounds might have on the hybridization reaction. Preferably, the concentration of Urea present in the reaction mixture will be approximately 0.01 to about 4M. The actual amount of Urea to be used must be determined for each different situation.

Guanidine HCl (GHCl) is another denaturing agent which can be added to the aqueous reaction mixture. This agent is useful to solubilize non-nucleic acid substances which may otherwise interfere with the hybridization reaction. Addition of GHCl to an aqueous reaction mixture optimized for both rate and extent of hybridization seen at specific times of incubation. A higher concentration of accelerating agent must be used in order to optimize the extent of hybridization when GHCl is present. Example 46 presents data concerning this. It is likely that the GHCl solubilizes nucleic acids to a certain extent and that more accelerating agent is needed to concentrate the nucleic acids for rapid hybridization. A similar situation occurs with the sodium phosphate system as seen in Example 46.

Regardless of which of the alternative methods is utilized to practice the method of the present invention, the nucleic acid precipitating agents are preferably selected from the group consisting of detergent, dihydroxybenzene, sodium dodecyl sulfate (SDS), sodium diisobutyl sulfosoccinate (SDIBSS), sodium tetradecyl sulfate (STDS), Sarkosyl, and the alkali metal salts and ammonium salts of $SO_4$, $PO_4$, Cl, and HCOO. It is also contemplated as being within the scope of the present invention to combine various members of this group in a single aqueous reaction solution. Additionally, it is also contemplated as being within the scope of the present invention to utilize a variety of detergent agents in addition to the organic compounds disclosed. Accordingly, those compounds specifically disclosed and claimed in the present invention are those which are currently known to be suitable for practicing the method of the present invention. Analogous compounds are therefore considered to be within the scope of the present invention.

It will be appreciated that the effective concentrations of nucleic acid precipitating agents necessary to practice the method of the present invention will vary with the amount of nucleic acid as well as with the size of the nucleic acid in the reaction solution and the pH of the solution as well as with the presence of other compounds. Accordingly, it is preferred that the concentrations will range from approximately 1M to 10M for the inorganic salt compounds and from approximately 5% by volume to approximately 95% by volume for the organic compounds. Additionally, it is preferred that the pH of the reaction solution will range from approximately 4 to 11.

Lastly, as discussed above, the preferred incubation temperature for the aqueous reaction solution should range from approximately room temperature to approximately 90° C.

The method of the present invention is suitable for bacterial, viral, mammlian and chemically synthesized nucleic acid. The completeness of the reaction will vary depending upon the concentration of the strong nucleic acid precipitating agent as well as on the amount of nucleic acid in the original reaction solution and on the composition of the reaction mixture. At low concentrations of nucleic acid, well over 90% of the single stranded nucleic acid will associate to form double stranded nucleic acid molecules. At higher nucleic acid concentrations, the completeness of the reaction will only be approximately 70% or less even though the rate of the reaction will be greatly increased. It should be noted that at very high concentrations of nucleic acid reactants, the rate of reaction will be accelerated to a lesser degree.

The amount of single stranded nucleic acid molecule reactants present in the aqueous reaction solution can range from an upward extreme approaching the solubility limit of the nucleic acid molecules to a lower extreme on the order of $10^{-9}$ micrograms. Interestingly, the reaction rate increase for high concentrations of DNA:DNA or DNA:RNA reactions is lower than that for low concentrations of DNA:DNA and RNA:RNA reactions. Thus, the method of the present invention is applicable to both high and low concentrations of reactants. Along these lines, preferred reaction solution volumes will be on the order of a milliliter or less to a fraction of a microliter. However, it should be emphasized that other reaction solution volumes are contemplated as being within the scope of the present invention. Additionally, while the presence of small quantities of protein and other cell components will not greatly interfere with the reaction of the method of the present invention, excess heterologous RNA or DNA or other cellular components will slow the reaction rate to various extents as well as affecting the completeness of the hygridization.

Detergents are useful to help minimize the effect of excess cell and other components on the reaction of the method of the present invention. Addition of detergents compatible with individual rate accelerating agents to reaction mixtures is helpful in this regard. Certain detergents greatly accelerate nucleic acid hybridization and are quite useful in this regard. The optimum rate accelerator concentration to be used for different nucleic acids is dependent on the variables discussed above.

It should also be noted that the greatly accelerated reaction rates have been achieved for nucleic acid molecules ranging from approximately 30 bases long to molecules on the order of $10^4$ bases long. However, the method of the present invention is contemplated as being applicable to nucleic acid molecules ranging from short molecules on the order of 10 to 15 bases long to longer molecules in excess of $10^4$ bases long.

The following examples are offered as being illustrative of the method of the present invention and not by way of limitation.

The methods of the invention described in the above examples have great significance in the area of detection and identification of a wide variety of different life forms in various types of samples. The said methods make it possible to detect and identify many life forms with a rapidity and sensitivity heretofore unattainable. The following examples illustrate this.

EXAMPLE 1

Method for Using Sodium Phosphate to Increase DNA:DNA Hybridization Rates

1. Mix thoroughly:

50 microliters of 0.17% SDS, $3 \times 10^{-3}$M, EDTA, containing 0.004 mcg of sonicated single strand $^3$H-E.Coli. DNA of about 300 to 700 bases in length.

+50 microliters of 4.8M sodium phosphate pH=6.8

2. Incubate the mixture at 76° C. and remove aliquots at specified times after the start. Dilute the aliquots into 0.14M PB 0.02% SDS and assay for hybridization using hydroxyapatite as described earlier.

The above procedure results in a rate increase of about 800 relative to the rate at the standard reference condition.

Such large rate increases can be attained with a variety of different volumes, concentrations of sodium phosphate, DNA concentrations, EDTA and SDS concentrations and temperatures of incubation.

EXAMPLE 2

Method for Using Sodium Sulfate to Increase DNA:DNA Rates

1. Mix thoroughly:
0.15 ml water containing 2 mcg of $^3$H-*E.Coli.* sonicated single strand DNA (300 to 700 bases long)
+0.85 ml of 2.25M Sodium sulfate.

2. Incubate the mixture at 77° C. and remove aliquots at specified times after the start. Dilute the aliquot into 1 ml 0.14M PB, 0.02% SDS and assay on HA as described earlier.

This procedure results in a rate increase of about 600 fold relative to the reference condition.

EXAMPLE 3

LiCl Rate Increase Method for DNA:DNA Hybridization

1. Mix thoroughly:
0.3 ml 9.16M Tris pH=7.8, containing about 10 mcg sonicated single strand 3H-*E.Coli.* DNA (about 300 to 700 bases long)
+0.2 ml 10M lithium chloride.

2. Incubate the mixture at 76° C. and remove aliquots at specified times after the start. Dilute the aliquot and assay for hybridization as described earlier.

This procedure results in a rate increase of about 600 relative to the reference condition.

EXAMPLE 4

Ammonium Sulfate Method for DNA:DNA Hybridization Rate Increase

A. Bacterial DNA

1. Mix thoroughly:
50 microliters of 0.2 Tris pH=7.8, containing about 5 mcg of sonicated single strand $^3$H-*E.Coli.* DNA (about 300 to 700 bases long);
+50 microliters of 4.0M Ammonium sulfate.

2. Incubate the mixture at 76° C. and remove aliquots at specified times after the start. Dilute the aliquot and assay for hybridization as described earlier.

This procedure resulted in a rate increase of about 700 relative to the reference condition.

EXAMPLE 5

B. Bacterial DNA: Ethanol Modification

The temperature at which the hybridization is conducted can be lowered dramatically by adding alcohol to the reaction mixture. Ethanol is soluble to about 20% in 2M Ammonium sulfate.

1. Mix thoroughly:
0.05 ml of 34% ethanol in water containing 0.4 mcg of sonicated single strand 3H-*E.Coli.* DNA (300 to 700 bases long).
+0.05 ml 4M ammonium sulfate, 0.01M EDTA, 0.01M PB pH=6.8

2. Incubate the mixture at 49° C. for appropriate times and remove aliquots. Dilute and assay the aliquots for hybridization as described earlier.

This procedure results in a rate increase of about 100 fold relative to the reference condition.

EXAMPLE 6

C Mammalian DNA: Low Concentration

1. Mix thoroughly: 0.1 ml of 0.02M EDTA containing 26 mcg of sonicated single strand $^3$H human DNA (about 400 to 800 bases long):
+0.1 ml 4M Ammonium sulfate, 0.1M PB pH=6.8

2. Incubate the mixture at 68° C. and at specified times remove aliquots. Dilute each aliquot and assay for hybridization as described earlier.

This procedure results in a rate increase of about 200 fold relative to the reference condition.

EXAMPLE 7

D. Mammalian DNA: Low concentration: Ethanol Modification

1. Mix thoroughly:
0.05 ml of 0.016M EDTA, 40% ethanol in water containing 26 mcg sonicated single strand $^3$H human DNA (about 400 to 800 bases long);
+0.05 ml 4M ammonium sulfate, 0.1M PB pH=6.8

2. Incubate the mixture at 49° C. and at specified times remove aliquots. Dilute each aliquot and assay it for hybridization as described earlier.

This procedure resulted in a rate increase of about 180 fold relative to the reference condition.

EXAMPLE 8

E. Mammalian DNA: High Concentration

1. Mix thoroughly:
0.025 ml of 0.04M EDTA in water containing 130 mcg of sonicated single strand human $^3$H DNA (about 400 to 800 bases long);
+0.025 ml 4M ammonium sulfate, 0.1M PB pH=6.8

2. Incubate the mixture at 68° C. and at specified times remove aliquots. Dilute each aliquot and assay for hybridization as described earlier.

This procedure results in a rate increase of about 90 fold relative to the reference condition.

EXAMPLE 9

F. Mammalian DNA: High Concentration: Ethanol Modification

1. Mix thoroughly:
0.0125 ml of 0.016M EDTA in water containing 40% ETOH and 65 mcg of sonicated single strand human $^3$H DNA (400 to 800 bases long);
+0.0125 ml 4M ammonium sulfate, 0.1M PB pH=6.8

2. Incubate the mixture at 49° C. and at specified times remove aliquots. Dilute each aliquot and assay it for hybridization as described earlier.

This procedure results in a rate increase of about 130 fold relative to the reference condition.

EXAMPLE 10

Purified RNA:DNA Hybridization Rate Increases with Sodium Phosphate

A. Excess RNA: 0.2 ml Volume

1. Thoroughly mix:
0.1 ml of 0.2% SDS, $10^{-3}$M EDTA in water containing $2 \times 10^{-3}$ mcg of Polio I RNA and $2 \times 10^{-4}$ mcg of $^3$H-cDNA ($^3$H-DNA complementary to Polio RNA, 300 to 600 bases long)
+0.1 ml 4.8M sodium phosphate pH=6.8

2. Incubate the mixture at 76° C. and at specified times remove aliquots. Dilute each aliquot and assay it for hybridization as described earlier.

This procedure results in a hybridization rate increase of 3300 fold over the rate in the standard reference condition of 60° C., 0.18M Na.

EXAMPLE 11

B. Excess RNA: 1 ml volume

1. Thoroughly mix:

0.5 ml $10^{-3}$ EDTA, 0.2% SDS containing $2 \times 10^{-3}$ mcg Polio I RNA and $2 \times 10^{-4}$ mcg of 300 to 600 base long Polio $^3$H-cDNA;

+0.5 ml 4.8M sodium phosphate pH=6.8

2. Incubate at 76° C. and at specified times remove aliquots. Dilute each aliquot and assay it for hybridization as described earlier.

This procedure results in a hybridization rate increase of 3300 fold over the reference condition rate.

EXAMPLE 12

C. Excess RNA: Plus Added Heterologous High Molecular Weight RNA

1. Thoroughly mix:

0.05 ml $10^{-3}$M EDTA, 0.4% SDS in water containing $2 \times 10^{-3}$ mcg Polio I RNA, $2 \times 10^{-4}$ mcg Polio I $^3$H-cDNA (300 to 600 bases long) and 5 mcg. of calf liver RNA;

+0.05 ml 5.1 sodium phosphate.

2. Incubate the mixture at 76° C. and at specified times remove aliquots. Dilute each aliquot and assay it for hybridization as described earlier.

This procedure resulted in a rate increase of 600 fold over the rate at the reference condition.

EXAMPLE 13

D. Excess DNA:

1. Thoroughly mix:

0.012 ml 0.012% Sarkosyl containing $1.5 \times 10^{-6}$ mcg of $^3$H-cDNA and $1.2 \times 10^{-6}$ ribosomal RNA from *Legionella pneumophila*. The $^3$H cDNA (100 to 300 bases long) is complementary to only about one third of the RNA. The cDNA/RNA ratio is about 4/1 for the complementary RNA and DNA sequences.

+0.02 ml of 4.8M sodium phosphate pH=6.8

2. Incubate the mixture at 76° C. and at specified times remove aliquots. Dilute each aliquot and assay it for hybridization.

This procedure results in a rate increase of greater than 3000 over the rate at the reference condition.

EXAMPLE 14

E. Excess DNA: Non Purified RNA

1. Thoroughly mix:

0.012 ml of $1.4 \times 10^{-3}$M EDTA, $1.4 \times 10^{-3}$ EGTA, 0.7% SDS, 0.3% Sarkosyl containing 10 mcg Proteinase K, $10^{-4}$ mcg of $^3$H-cDNA (100 to 300 bases long) complementary to *Legionella pneumophila* ribosomal RNA and 4400 *Legionella pneumophila* bacteria which contain about $6 \times 10^{-5}$ mcg. of ribosomal RNA.

+0.02 ml of 4.8M sodium phosphate pH=6.8

2. Incubate the mixture at 76° C. and at specified times remove aliquots. Dilute each aliquot and assay each aliquot for hybridization as described earlier.

This procedure results in a rate increase of greater than 150 fold over the rate in the reference condition.

EXAMPLE 15

F. Excess RNA: Non Purified RNA

1. Thoroughly mix:

0.012 ml of 0.16% Sarkosyl containing $10^{-5}$ mcg of $^3$H-cDNA (100 to 300 bases long) complementary to *E. Coli* ribosomal RNA and 5000 *E. Coli* bacteria which contain about $7 \times 10^{-5}$ mcg ribosomal RNA.

+0.02 ml of 4.8M sodium phosphate pH=6.8

2. Incubate the mixture at 76° C. and at specified times remove aliquots. Dilute each aliquot and assay it for hybridization as described earlier.

This procedure results in a rate increase of greater than 100 fold over the rate at the reference condition.

EXAMPLE 16

RNA:DNA Hybridization Rate Increase Promoted by Sodium Sulfate

1. Mix well:

0.023 ml of $10^{-3}$M EDTA, 0.1% SDS containing $2 \times 10^{-3}$ mcg Polio I RNA and $2 \times 10^{-4}$ mcg $^3$H-cDNA (300 to 600 bases long) which is complementary to Polio I RNA.

+0.178 ml. 2.25M sodium sulfate.

2. Incubate at 76° C. and at specified times remove aliquots. Dilute aliquot and assay it for hybridization as described earlier.

This procedure resulted in a rate increase of over 3000 relative to the reference rate.

EXAMPLE 17

RNA:DNA Hybridization Rate Increase Promoted by Ammonium Sulfate

1. Mix well:

0.1 ml of 0.2% SDS, $10^{-3}$M EDTA containing $2 \times 10^{-3}$ mcg of Polio I RNA and $2 \times 10^{-4}$ mcg of $^3$H-cDNA (300 to 600 bases long) which is complementary to Polio I RNA +0.1 ml of 4M ammonium sulfate.

2. Incubate at 77° C. and at specified times remove aliquots. Dilute each aliquot and assay it for hybridization as described earlier.

This procedure resulted in a rate increase of about 1500 relative to the reference condition rate.

EXAMPLE 18

RNA:RNA Hybridization Rate Increase Promoted by Ammonium Sulfate

1. Mix well:

0.1 ml 0.2% SDS, $10^{-3}$M EDTA containing $4 \times 10^{-3}$ mcg VSV RNA and $2 \times 10^{-4}$ mcg $^{125}$I-cRNA (about 300 to 800 bases long) which is complementary to VSV RNA.

+0.1 ml 4.4M ammonium sulfate.

2. Incubate at 87° C. and at specified times remove aliquots. Dilute each aliquot and assay it for hybridization by a standard ribonuclease technique.

This procedure resulted in a rate increase of over 1000 relative to the 0.18M Na rate.

EXAMPLE 19

RNA:RNA Hybridization Rate Increase Promoted by Sodium Phosphate

1. Mix well:

0.1 ml 0.2% SDS, $10^{-3}$M EDTA containing $4\times10^{-3}$ mcg VSV RNA and $2.10^{-4}$ mcg VSV $^{125}$I-cRNA which is complementary to VSV RNA.

+0.1 ml 4.8M sodium phosphate.

2. Incubate at 83° C. and at specified times remove aliquots. Dilute each aliquot and assay it for hybridization by a standard ribonuclease technique.

This procedure results in a rate increase of greater than 500 relative to the reference condition rate.

EXAMPLE 20

Method For Using Sodium Dodecyl Sulfate To Increase DNA:RNA Hybridization Rates

This example shows that a greatly accelerated hybridization rate occurs at 28.5% (W/V) SDS when probe is in excess over purified RNA.

A. Excess Probe Plus Homologous RNA

1. Thoroughly mix:

1 μl solution containing $01.6\times10^{-4}$ micrograms Legionella Ribosomal RNA (rRNA).

1 μl 5M Sodium Phosphate Buffer (pH=6.8)(PB).

3 μl probe solution containing $10^{-4}$ micrograms of $I^{125}$-cDNA complementary to about 1/5 of the Legionella rRNA 95 μl 30% (W/V) sodium dodecyl sulfate in $H_2O$.

2. Incubate the mixture at 72° C. and at specific times remove aliquots. Dilute each aliquot and assay for hybridization as described earlier.

This procedure resulted in a rate increase of 100–200 fold over the rate at the reference condition.

EXAMPLE 21

B. Excess Probe Hybridization

This example shows that a greatly accelerated hybridization rate occurs at 31.4% (W/V) SDS when probe is in excess over purified RNA.

1. Thoroughly mix:

1 μl of solution containing $1.6\times10^{-4}$ micrograms of Legionella Ribosomal RNA.

6 μl $H_2O$.

1 μl 5M Sodium Phosphate Buffer (pH=6.8)(PB)

2 μl probe solution containing $10^{-4}$ micrograms of $I^{125}$-cDNA complementary to about 1/5 of the Legionella Ribosomal RNA sequence.

90 μl 34.9% (W/V) sodium dodecyl sulfate in $H_2O$.

2. Incubate the mixture at 72° C. and at specified times remove aliquots. Dilute each aliquot and assay for hybridization as described earlier.

This procedure resulted in a rate increase of 150–200 fold over the rate at the reference condition.

EXAMPLE 22

C. Excess RNA Hybridization:

This example shows that a greatly accelerated hybridization rate occurs at 31.4% (W/V) SDS when purified RNA is in excess.

1. Thoroughly mix:

2 μl solution containing $3.2\times10^{-4}$ micrograms Legionella Ribosomal RNA.

1 μl $H_2O$.

1 μl 5.0M Sodium Phosphate Buffer (pH=6.8)(PB).

2 μl probe solution containing $2.5\times10^{-5}$ micrograms of $I^{125}$-cDNA complementary to the Legionella Ribosomal RNA.

95 μl 34.9% (W/V) sodium dodecyl sulfate in $H_2O$.

2. Incubate the mixture at 72° C. and at specified times remove aliquots. Dilute each aliquot and assay for hybridization as described earlier.

This procedure resulted in a rate increase of 150–200 fold over the rate at the reference condition.

EXAMPLE 23

D. Detection of Legionella Bacteria Present in a Liquid Sample.

This example shows that a greatly accelerated hybridization rate occurs at 31.4% (W/V) SDS when bacteria are isolated out of a liquid sample and lysed. Accelerated hybridization occurs even in the presence of non-nucleic acid bacterial cell components.

1. (a) Centrifuge a sample known to contain Legionella organisms at 14,000 xg for 10 minutes, and then remove the supernatant.

(b) Resuspend the pellet in a lysing buffer and lyse the bacteria, thus freeing the nucleic acid.

(c) Thoroughly mix:

1 μl of lysed bacteria solution in 5% sodium dodecyl sulfate, 0.05 m Tris buffer pH=8.2.

1 μl $H_2O$.

1 μl 5.0M Sodium Phosphate Buffer (PB)

2 μl probe solution containing $5\times10^{-5}$ micrograms of $I^{125}$-cDNA complementary to the Legionella Ribosomal RNA.

2. Incubate the mixture at 72° C. and at specified times remove aliquots. Dilute each aliquot and assay for hybridization as described earlier.

This procedure resulted in a rate increase of 100–200 fold over the rate at the reference condition.

EXAMPLE 24

E. Detection of Legionella Bacteria in a Sputum Sample Known To Contain Such Bacteria This example shows that a greatly accelerated hybridization rate occurs at 23.4% (W/V) SDS when the bacteria have been isolated out of a clinical sample, lysed and hybridized with no purification of RNA.

1. (a) Solubilize 1 ml sputum by adding 0.1 ml of 0.1M DTT and centrifuge for 10' at 14,000 xg to pellet bacteria. Discard the supernatant.

(b) Resuspend pellet in lysing buffer and lyse Legionella bacteria to free nucleic acids.

(c) Thoroughly mix:

30 μl of lysing solution (containing about 8000 lysed Legionella bacteria) composed of 11% sodium dodecyl sulfate (W/V); $3\times10^{-3}$M EDTA; 0.003M Tris unbuffered.

1 μl 5M Sodium Phosphate Buffer (pH=6.8)(PB).

2 μl probe solution containing $10^{-4}$ micrograms of $I^{125}$-cDNA complementary to the Legionella rRNA.

67 μl 34.9% (W/V) SDS.

2. Incubate the mixture at 72° C. and at specified times remove aliquots. Dilute each aliquot and assay for hybridization as described earlier.

This procedure resulted in a rate increase of 100–200 fold over the rate at the reference condition.

EXAMPLE 25

F. Detection of Legionella Bacteria in a Sputum Sample Known to Contain Such Bacteria This example shows that a greatly accelerated hybridization rate occurs at 23.4% (W/V) SDS when the clinical sample is assayed directly and the hybridization is done in the presence of the sputum components.

1. (a) Mix a sputum sample known to contain Legionella bacteria with an equal volume of a lysing agent solution (33% SDS, 0.01 m unbuffered Tris, 0.01 m EDTA, 0.01 m EGTA). Incubate at 72° C. 15 minutes.
   (b) Mix thoroughly:
   30 μl of solution from 1(a).
   1 μl 5M Sodium Phosphate Buffer (pH=6.8)(PB).
   2 μl probe solution containing $10^{-4}$ micrograms of of $I^{125}$-cDNA complementary to the Legionella rRNA.
   67 μl 34.9% (W/V) SDS in $H_2O$.

2. Incubate the mixture at 72° C. and at specified times remove aliquots. Dilute each aliquot and assay for hybridization as described earlier.

This procedure resulted in a rate increase of 100–200 fold over the rate at the reference condition.

EXAMPLE 26

Method For Using Sodium Tetradecyl Sulfate (STDS) To Increase Nucleic Acid Hybridization Rate This example shows a greatly accelerated rate occurs at 24.3% (W/V) STDS when purified RNA is used.

A. RNA:DNA Hybridization in STDS.
1. Thoroughly mix:
   1 μl of a solution containing $1.7 \times 10^{-4}$ micrograms of Legionella rRNA.
   7 μl $H_2O$.
   2 μl probe solution containing $10^{-4}$ micrograms of $I^{125}$-cDNA complementary to Legionella rRNA.
   90 μl 27% (W/W) STDS, 0.03M PB; final pH=7.

2. Incubate the mixture at 72° C. and at specified times remove aliquots. Dilute each aliquot and assay for hybridization as described earlier.

This procedure resulted in a rate increase of at least 500–1000 fold over the rate at the reference condition.

EXAMPLE 27

B. RNA:DNA Hybridization in STDS+UREA. Addition of Urea Increases The Extent of Hybridization This example shows that a greatly accelerated rate occurs at 24.3% (W/W) STDS when Urea is present in the reaction mix.

1. Mix thoroughly:
   1 μl solution containing $1.7 \times 10^{-4}$ micrograms of Legionella rRNA.
   2 μl $H_2O$.
   5 μl 10M Urea.
   2 μl probe solution containing $10^{-4}$ micrograms of $I^{125}$-cDNA complementary to the Legionella rRNA.
   90 μl 27% (W/W) STDS, 0.03M PB: final pH=7.

2. Incubate the mixture at 72° C. and at specified times remove aliquots. Dilute each aliquot and assay for hybridization as described earlier.

This procedure resulted in a rate increase of at least 500–1000 fold over the rate at the reference condition. In addition a greater extent of hybridization is seen with urea present.

EXAMPLE 28

A. Hybridization Rate Increase Prompted by Sodium Diisobutyl Sulfosuccinate (SDIBSS)

This example shows that a greatly accelerated rate occurs at 41.4% (W/W) SDIBSS when phosphate buffer (PB) is used to adjust the SDIBSS pH to about 7.

a. RNA:DNA hybridization
1. Mix well:
   1 μl of a solution containing $1.7 \times 10^{-4}$ micrograms of Legionella rRNA.
   2 μl 5M PB.
   2 μl $I^{125}$-cDNA complementary Legionella rRNA.
   4 μl $H_2O$.
   92 μl 45% (W/W) SDIBSS.

2. Incubate at 72° C. and at specified times remove aliquots. Dilute each aliquot and assay for hybridization as described earlier.

This procedure resulted in a rate increase of 100–200 fold over the rate at the reference condition.

EXAMPLE 29

B. RNA:DNA Hybridization in SDIBSS

This example shows that a greatly accelerated rate occurs at 33.8% (W/W)SDIBSS when phosphate buffer is used to adjust the SDIBSS pH to about 7.

1. Mix well:
   1 μl solution containing $1.7 \times 10^{-4}$ micrograms of Legionella rRNA.
   2 μl 5M PB.
   2 μl $I^{125}$-cDNA complementary to Legionella rRNA.
   20 μl $H_2O$
   75 μl SDIBSS 45% (W/W).

2. Incubate at 72° C. and at specified times remove aliquots. Dilute each aliquot and assay it for hybridization as described earlier.

This procedure results in a hybridization rate increase of 100–200 fold over the reference condition rate.

EXAMPLE 30

C. RNA:DNA Hybridization in SDIBSS

This example shows that a greatly accelerated rate occurs at 38.2% (W/W)SDIBSS when phosphate buffer is used to adjust the SDIBSS pH to about 7.

1. Mix well:
   1 μl of solution containing $1.7 \times 10^{-4}$ micrograms Legionella rRNA.
   2 μl 5M PB
   2 μl $I^{125}$-cDNA complementary to Legionella rRNA.
   10 μl $H_2O$.
   85 μl 45% (W/W) SDIBSS.

2. Incubate at 72° C. and at specified times remove aliquots. Dilute each aliquot and assay it for hybridization as described earlier.

This procedure results in a hybridization rate increase of 100–200 fold over the reference condition rate.

EXAMPLE 31

D. RNA:DNA Hybridization in SDIBSS

A greatly accelerated rate occurs when unbuffered Tris is used to adjust the SDIBSS pH to about 9.

1. Mix well:
   1 μl of solution containing $1.7 \times 10^{-4}$ micrograms of Legionella rRNA.
   7 μl 1M Tris, unbuffered.
   2 μl $I^{125}$-cDNA complementary to Legionella rRNA.
   90 μl 45% (W/W) SDIBSS.

2. Incubate the mixture at 72° C. and at specified times remove aliquots. Dilute each aliquot and assay it for hybridization as described earlier.

This procedure resulted in a rate increase of 100–200 fold over the rate at the reference condition.

EXAMPLE 32

E. RNA:DNA Hybridization In A Mixture of Sodium Dodecyl Sulfate (SDS) and SDIBSS A greatly accelerated rate occurs in a mixture of SDS and SDIBSS.

1. Mix well:
   1 μl of solution containing $1.7 \times 10^{-4}$ micrograms Legionella rRNA.
   7 μl 1M Tris unbuffered.
   2 μl $I^{125}$-cDNA complementary to Legionella rRNA.
   45 μl 34.9% (W/V) SDS.
   45 μl 45% (W/V) SDIBSS.
2. Incubate the mixture at 72° C. and at specified times remove aliquots. Dilute each aliquot and assay it for hybridization as described earlier.

This procedure resulted in a rate increase of 100–200 fold over the rate at the reference condition.

EXAMPLE 33

F. RNA:DNA Hybridization In SDIBSS In The Presence of Heterologous RNA

A greatly accelerated rate occurs in the presence of a high concentration (56 micrograms/ml) of heterologous RNA.

1. Mix well:
   1 μl of solution containing $1.7 \times 10^{-4}$ micrograms Legionella rRNA.
   3 μl of solution containing 5.6 micrograms of heterologous bacterial RNA.
   4 μl 1M Tris, unbuffered.
   2 μl $I^{125}$-cDNA complementary to Legionella rRNA.
   90 μl 45% (W/W) SDIBSS.
2. Incubate the mixture at 72° C. and at specified times remove aliquots. Dilute each aliquot and assay it for hybridization as described earlier.

This procedure resulted in a rate increase of at least 100–200 fold over the rate at the reference condition.

EXAMPLE 34

G. Detection of Legionella Bacteria In Sputum By RNA:DNA Hybridization In SDIBSS A greatly accelerated rate occurs when bacteria are isolated from sputum, lysed and hybridized in SDIBSS. Hybridization occurred in SDIBSS even in the presence of non-nucleic acid cellular components.

1. (a) Solubilize 1 ml of sputum by adding 0.1 ml 0.25, DTT and centrifuge the mixture at 14,000 x g for 10' to pellet bacteria. Discard supernatant.
   (b) Resuspend pellet in one third of its volume of lysing buffer (33% SDS, 0.01M EDTA, 0.01M Tris, unbuffered) and incubate at 72° C. for 15' to lyse bacteria.
   (c) Mix well:
   2 μl 5M PB.
   4 μl $I^{125}$-cDNA complementary to Legionella rRNA.
   30 μl 45% (W/W) DBISS.
   (d) Add mixture (c) to mixture (b) and thoroughly mix.
2. Incubate the mixture at 72° C. and at specified times remove aliquots. Dilute each aliquot and assay it for hybridization as described earlier.

This procedure resulted in a rate increase of 100–200 fold over the rate of reference condition.

EXAMPLE 35

H. Detection of Legionella Bacteria In A Liquid Sample By RNA:DNA Hybridization In SDIBSS A greatly accelerated rate occurs when the bacteria are isolated from a non-clinical sample and hybridized in SDIBSS. A separate lysing incubation step was not performed.

1. (a) Prefilter the liquid sample known to contain Legionella to remove large particles.
   (b) Mix well:
   30 μl solution of solution containing Legionella bacteria.
   15 μl 33% SDS, 0.01M Tris, unbuffered, 0.01M EDTA.
   1.8 μl 5M PB.
   5 μl $I^{125}$-cDNA complementary to Legionella rRNA.
   190 μl 45% (W/W) SDIBSS.
2. Incubate at 72° C. and at specified times remove aliquots. Dilute each aliquot and assay it for hybridization as described earlier.

This procedure results in a hybridization rate increase of 100–200 fold over the reference condition rate.

EXAMPLE 36

I. RNA:DNA Hybridization In The Presence of SDIBSS and Urea

A greatly accelerated rate occurs in a mixture of SDIBSS and Urea.

1. Mix well:
   1 μl of solution containing $1.7 \times 10^{-4}$ micrograms of Legionella rRNA.
   2 μl $H_2O$.
   5 μl 10M Urea.
   90 μl SDIBSS 45% (W/W).
2. Incubate at 72° C. and at specified times remove aliquots. Dilute each aliquot and assay it for hybridization as described earlier.

This procedure results in a hybridization rate increase of at least 200 fold over the reference condition rate.

EXAMPLE 37

J. RNA:DNA Hybridization In SDIBSS and Urea

A greatly accelerated rate occurs in a mixture of SDIBSS and Urea.

1. Mix well:
   2 μl solution containing $3.4 \times 10^{-4}$ micrograms of Legionella rRNA.
   1 μl 5M PB.
   2 μl $I^{125}$-cDNA complementary to Legionella rRNA.
   25 μl 27% (W/W) SDIBSS, 8M Urea.
   70 μl 45% (W/W) SDIBSS.
2. Incubate at 72° C. and at specified times remove aliquots. Dilute each aliquot and assay it for hybridization as described earlier.

This procedure results in a hybridization rate increase of 100–200 fold over the reference condition rate.

EXAMPLE 38

K. RNA:DNA Hybridization In The Presence Of SDIBSS and NaSCN

A greatly accelerated rate occurs in a mixture of SDIBSS and sodium thiocyanate.

1. Mix well:
   2 μl solution containing $3.4 \times 10^{-4}$ micrograms of Legionella rRNA.

1 µl 5M PB.
2 µl I[125]-cDNA complementary to Legionella rRNA.
5 µl 10.5M NaSCN.
90 µl 45% (W/W) SDIBSS.

2. Incubate at 72° C. and at specified times remove aliquots. Dilute each aliquot and assay it for hybridization as described earlier.

This procedure results in a hybridization rate increase of 100-200 fold over the reference condition rate.

EXAMPLE 39

L. RNA:DNA Hybridization In Mixtures Of SDIBSS, Urea and NaSCN

A greatly accelerated rate occurs in the presence of SDIBSS, sodium thiocyonate and Urea.

1. Mix well:
2 µl of solution containing $3.4 \times 10^{-4}$ micrograms of Legionella rRNA.
1 µl 5M PB.
2 µl I[125]-cDNA complementary to Legionella rRNA.
5 µl 4M Urea, 4M NaSCN, 0.05M DTT, 0.03M Hcl.
90 µl 45% (W/W) SDIBSS.

2. Incubate at 72° C. and at specified times remove aliquots. Dilute aliquot and assay it for hybridization as described earlier.

This procedure results in a hybridization rate increase of at least 100-200 fold over the reference condition rate.

The following examples concern the rapid and sensitive detection of three medically important bacteria, each of which causes disease in humans.

A. Bacteria in the Mycobacteria group cause a variety of human disease. Prominent among them are tuberculosis and leprosy. Current diagnostic methods use the culture approach for the detection and identification of these bacteria. A growth step is necessary to amplify the bacteria so they can be detected and differential growth methods are used to identify these bacteria. This method of diagnosis is labor intensive and very slow. As it is important to know as soon as possible if the patient is infected with Mycobacteria in order to start the proper anti-microbial therapy, this method of diagnosis is labor intensive and very slow.

With current methods it takes 1-8 weeks to obtain a definitive diagnosis for Mycobacteria. The assay described in Example 44 takes about 2-3 hours to perform and does not require a growth step. Thus the method of the invention allows the design of a test for Mycobacteria which is over 100 times faster than the current methods, does not require a growth step, is much less labor intensive and is less expensive. In addition, the rapidity of the test will make rapid treatment of the disease possible with incalculable benefits to the patients.

B. The bacteria Mycoplasma pneumoniae also causes disease in humans. Culture methods are currently used for diagnosis and a definitive diagnosis generally takes from 1-2 weeks.

The assay described in Example 42 takes less than 2 hours to perform and does not require a growth step. Thus the method of the invention allows the design of a test for Mycoplasma pneumoniae which is about 100 times faster than the current methods and has other advantages and benefits similar to those described in A above.

C. Legionella bacteria also cause human disease. Current recommended diagnostic procedures involve culture methods. Such methods generally yield a definitive answer in about 3 days but can take a week or longer.

The assay described in Example 44 takes less than 2 hours to perform, does not require a growth step, is about 20 times faster than current methods and has other advantages and benefits similar to those described in A above.

EXAMPLE 40

M. Detection Of Legionella Bacteria In Sputum Sample By RNA:DNA Hybridization In SDIBSS, Urea and SDS A greatly accelerated rate occurs when sputum is assayed directed in a mixture of SDIBSS, SDS and Urea.

1. (a) Mix well:
3 µl sputum.
6 µl 17% SDS, 0.01M Tris (unbuffered), 0.01M EDTA. Incubate at 72° C. for 15'.

(b) Mix well:
3 µl 1(a) solution.
2 µl H$_2$O.
3 µl 10M Urea.
2 µl I[125]-cDNA complementary to Legionella rRNA.
90 µl 45% (W/W) SDIBSS.

2. Incubate at 72° C. and at specified times remove aliquots. Dilute each aliquot and assay it for hybridization as described earlier.

This procedure results in a hybridization rate increase of 100-200 fold over the reference condition rate.

EXAMPLE 41

N. Detection of Legionella Bacteria In Sputum Sample By RNA:DNA Hybridization In SDIBSS, Urea, SDS Mixes An example of the rapid detection of Legionella bacteria in a sputum sample by using a mixture of SDIBSS, SDS, and Urea to greatly accelerate hybridization rate.

1. (a) Mix well:
20 µl of sputum.
80 µl 5M Urea, 4M NaSCN, 0.05M Tris (unbuffered) and centrifuge for 10 minutes at 14,000 x g. Discard supernaye.

(b) Add 25 µl 11% SDS, 3.3M Urea, 0.007M EDTA, 0.05M Tris (unbuffered) to pellet and resuspend. Incubate at 72° C. for 15 minutes.

(c) Mix well:
5 µl solution for 1(b).
2 µl I[125]-cDNA complementary to Legionella rRNA.
3 µl 10M Urea
90 µl 45% (W/W) SDIBSS.

2. Incubate the mixture at 72° C. for one hour and assay for hybridization as described.

This procedure resulted in a rate increase of 100-200 over the rate at the reference condition.

EXAMPLE 42

O. Detection of Mycoplasma Pneumonia Bacteria In A Throat Swab Sample By RNA:DNA Hybridization In SDIBSS An example of the use of the SDIBSS system for rapid detection of *Mycoplasma pneumoniae* in a clinical sample.

1. (a) Resuspend throat swab material in a suitable solution which is compatible with the bacteria of interest.

(b) Centrifuge the solution at 13,000 x g for 10 minutes. Discard supernatant.

(c) Resuspend the pellet in 300 μl of 45% (W/W) SDIBSS containing 3% SDS, 0.03M PB, (PH=6.8), $10^{-3}$M EDTA, $10^{-3}$M EDTA, $10^{-3}$M EGTA and $I^{125}$-cDNA complementary to *M. pneumonia* rRNA.

2. Incubate the mixture at 72° C. for one hour and assay for hybridization as described.

This procedure resulted in a rate increase of 100-200 fold over the rate at the reference condition.

EXAMPLE 43

A. Detection Of The Presence Of Mycoplasma In A Tissue Culture By Means Of RNA:DNA Hybridization In SDIBSS An example of the use of the Sodium Phosphate system for the rapid detection of Mycoplasma infection of tissue culture is disclosed.

1. (a) Centrifuge 50 μl of tissue culture media from a baby hamster kidney cell culture for 5 minutes at 12,000 x g. Discard the supernatant.

(b) Resuspend the pellet in 100 μl of 0.15M NaCl.

(c) Mix well:

45 μl solution (b).

5 μl 5% Sarkosyl, $10^{-2}$M EDTA, $10^{-2}$M EGTA, 0.96M PB, 0.01 micrograms/ml of 3H-cDNA complementary to *Mycoplasma hominis* rRNA.

65 μl 4.8M PB.

2. Incubate at 72° C. for one hour and assay for hybridization as described.

This procedure results in a hybridization rate increase of 100-200 fold over the reference condition rate.

EXAMPLE 44

B. Detection Of Mycobacteria In A Sputum Sample By RNA:DNA Hybridization In SDIBSS This is an example of the use of the SDIBSS system for the rapid detection of Mycobacteria in a clinical sample.

1 (a) Liquefy sputum and centrifuge solution to pellet Mycobacteria discard supernatant.

(b) Suspend pellet in 40 μl of 3.3% SDS and add 50 μl of glass beads (0.2-0.3 mm)(Dyno-Mill brand), sonicate 10 minutes in a mettler M4 ultrasonic cleaner.

(c) Mix well:

Solution from b).

100 μl 45% (W/W) SDIBSS.

176 μl 43.5% (W/W) SDIBSS, 0.07M PB, $I^{125}$-cDNA ($10^{-2}$ micrograms/ml) complementary to Mycobacteria rRNA.

2. Incubate the mixture at 72° C. for one hour and assay for hybridization as described.

This procedure reselted in a rate increase of 100-200 fold over the rate at the reference condition.

EXAMPLE 45

C. RNA:DNA Hybridization In A Mixture Of Urea and Sodium Phosphate

A greatly accelerated rate occurs in a mixture of Sodium Phosphate and Urea.

1. Mix well:

10 μl of solution containing 25,000 lysed Legionella bacteria. Total Legionella rRNA equalled $5 \times 10^{-4}$ micrograms. Solution composition was 1.3% SDS, 0.03M Tris pH=8.2, 0.37M NaCl $3.3 \times 10^{-4}$M EDTA, 0.66 milligrams/ml Proteinase K.

10 μl H₂O.

5 μl $I^{125}$-cDNA complementary to Legionella rRNA.

15 μl 10M Urea.

88 μl 5M PB.

2. Incubate the mixture at 72° C. and at specified times remove aliquots. Dilute each aliquot and assay it for hybridization as described earlier.

Little difference in rate or extent of hybridization was seen between this reaction and a control reation in which water was substituted for the Urea.

EXAMPLE 46

A. Effect of GHCl on RNA:DNA Hybridization in (NH₄)SO₄

| Concentration of (NH₄)So₄ in Reaction | Concentration of of GHCl in Reaction | Relative Extent of Hybridization |
|---|---|---|
| 2.2M | 0 | 100% |
| 2.2M | 1.45M | 13% |
| 2.4M | 1.28M | 35% |
| 2.6M | 1.1M | 46% |
| 2.75M | 1.0M | 105% |
| 3.0M | 0.8M | 96% |

B. Effect of GHCl on RNA:DNA Hybridization In Sodium Phosphate (PB)

| Concentration of (NH₄)So₄ in Reaction | Concentration of of GHCl in Reaction | Relative Extent of Hybridization |
|---|---|---|
| 3.1M | 0 | 100% |
| 3.1M | 1.45M | 36% |
| 3.3M | 1.25M | 71% |
| 3.53M | 1.1M | 90% |
| 3.75M | .92M | 95% |
| 3.9M | 0.8M | 114% |

EXAMPLE 47

Detection Of Legionella Bacteria In A Liquid Sample By RNA:DNA Hybridization In SDIBSS and Amphyl (Sold By National Laboratories): Active Ingredients In Amphyl, 10.5% 0-Phenylphenol, 5% 0-Benzo-P-Chlorophenol, 84.5% Inert Ingredients A greatly accelerated rate occurs in a mixture of Sodium Phosphate and Amphyl, a bactericidal agent.

1. Mix well:

2 μl solution containing $1.2 \times 10^4$ intact Legionella bacteria.

12 μl solution containing 4% Amphyl and radioactive cDNA complementary to Legionella rRNA.

18 μl 4.8M PB.

2. Incubate at 72° C. and at specified times remove aliquots. Dilute each aliquot and assay it for hybridization as described earlier.

This example demonstrates that the rRNA of Legionella bacteria is made available for hybridization by adding Amphyl to the reaction mixture. No pre-cracking of the bacteria is necessary.

In closing, it should be understood that the embodiments of the present invention disclosed herein are illustrative of the principles of the invention and that other modifications, nucleic acid precipitating agents or nucleic acid denaturing agents may be employed which are within the scope of the invention. How ever, the methods disclosed and described herein are preferred. Accordingly, the present invention is not limited to that precisely as disclosed and described.

What is claimed is:

1. A method for the formation of a double-stranded nucleic acid molecule from separate single-stranded nucleic acid molecules wherein the rate of formation is increased at least 100 times over the rate of formation of a double-stranded nucleic acid molecule from the same single-stranded nucleic acid molecules in a solution using 0.18M NaCl at 60° C. at the same pH, said method comprising the steps of:

preparing an aqueous reaction solution containing, in solution, a first quantity of a first single-stranded nucleic acid molecule and a second quantity of a second single-stranded nucleic acid molecule, said second single-stranded nucleic acid molecule having base sequences complementary to sequences of said first single-stranded nucleic acid molecule so as to allow for the formation of the double-stranded molecule, and a concentration of at least one nucleic acid precipitating agent dissolved therein consisting essentially of an amount sufficient to precipitate said first and second single-stranded nucleic acid molecules so as to increase said rate of formation at least 100 times the formation rate for the same double-stranded nucleic acid molecule in said reaction solution, comprising 0.18M NaCl in said reaction solution in place of said agent, at 60° C.; and incubating said aqueous reaction solution at a temperature at which reassociation can occur.

2. A method for the formation of a double-stranded nucleic acid molecule from separate single-stranded nucleic acid molecules wherein the rate of formation is increased at least 100 times over the rate of a formation of a double-stranded nucleic acid molecule from the same single-stranded nucleic acid molecules in solution using 0.18M NaCl at 60° C. at the same pH, said method comprising the steps of:

preparing an aqueous reaction solution containing, in solution, a first quantity of a first single-stranded nucleic acid molecule and a second quantity of a second single-stranded nucleic acid molecule, said second single-stranded nucleic acid molecule having base sequences complementary to base sequences of said first single-stranded nucleic acid molecule so as to allow for the formation of the double-stranded molecule mixing said aqueous reaction solution with a second solution having at least one nucleic acid precipitating agent, such that the resulting mixture has a concentration of said nucleic acid precipitating agent dissolved therein consisting essentially of an amount sufficient to precipitate said first and second single-stranded nucleic acid molecules so as to increase the rate of formation at least 100 times the formation rate for the same double-stranded nucleic acid molecule in said reaction solution comprising 0.18M NaCl in said reaction solution in place of said agent, at 60° C. and;

incubating the resulting mixture at a temperature at which reassociation can occur.

3. A method for forming a double-stranded nucleic acid molecule from a first and second single-stranded nucleic acid molecule; wherein said first and second nucleic acid molecules comprise first and second nucleic acid sequences respectively which are sufficiently complementary to cause said first and second nucleic acid molecules to hybridize at a first rate, to form the double-stranded nucleic acid molecule, in an aqueous solution comprising 0.18M NaCl and no other salt at 60° C., comprising the steps of:

(a) providing an aqueous solution comprising said first and second nucleic acid molecules, and a concentration of a nucleic acid precipitating agent in an amount sufficient to precipitate said first and second nucleic acid molecules at 60° C. and thereby cause said first and second nucleic acid molecule to hybridize at a second rate, said second rate being at least 100 times said first rate, and (b) incubating said aqueous solution at a temperature at which said first and second nucleic acid molecules hybridize at a rate at least 100 times said first rate.

4. The method of claim 1 or 3 wherein said nucleic acid precipitating agent is selected from the group consisting of detergent, dihydroxybenzene, sodium dodecyl sulfate, sodium diisbutyl sulfosuccinate, sodium tetradecyl sulfate, N-lauroylsarcosine sodium salt and the alkali metal salts and ammonium salts of $SO_4$, $PO_4$, Cl, and HCOO.

5. The method of claim 1 or 3 wherein said concentration ranges from about 1M to about 10M.

6. The method of claim 1 or 3 wherein said reaction solution also contains a sufficient concentration of a nucleic acid denaturing agent to lower the $T_m$ of the hybrid formed from the first and second nucleic acid molecules.

7. The method of claim 6 wherein said concentration of nucleic acid denaturing agent ranges from about 5% by volume to about 95% by volume.

8. The method of claim 6 wherein said nucleic acid denaturing agent is alcohol ranging in concentration from about 10% by volume to 20% by volume and said nucleic acid precipitating agent is $(NH_4)_2SO_4$.

9. The method of claim 1 or 3 wherein the pH of said aqueous reaction solution ranges from about 4 to about 11.

10. The method of claim 1 or 3 wherein said temperature ranges from about room temperature to about 90° C.

11. The method of claim 1 or 2 or 3 wherein said nucleic acid precipitating agent is sodium phosphate.

12. The method of claim 1 or 2 or 3 wherein said nucleic acid precipitating agent is $NaSO_4$.

13. The method of claim 1 or 2 or 3 wherein said nucleic acid precipitating agent is LiCl.

14. The method of claim 1 or 2 or 3 wherein said nucleic acid precipitating agent is $(NH_4)_2SO_4$.

15. The method of claim 1 or 2 or 3 wherein said nucleic acid precipitating agent is 13 volume % to 30 volume % N-lauroylsarcosine sodium salt.

16. The method of claim 1 or 2 or 3 wherein said nucleic acid precipitating agent is sodium dodecyl sulfate.

17. The method of claim 1 or 2 or 3 wherein said nucleic acid precipitating agent is sodium dissobutyl sulfosuccinate.

18. The method of claim 1 or 2 or 3 wherein said nucleic acid precipitating agent is sodium tetradecyl sulfate.

19. The method of claim 2 wherein said nucleic acid precipitating agent is selected from the group consisting of detergent, dihydroxybenzene, sodium dodecyl sulfate, sodium diisbutyl sulfosuccinate, sodium tetradecyl sulfate, N-lauroylsarcosine sodium salt and the alkali metal salts and ammonium salts of $SO_4$, $PO_4$, Cl, and HCOO.

20. The method of claim 2 wherein said concentration ranges from about 1M to about 10M.

21. The method of claim 2 wherein said aqueous reaction solution also contains a sufficient concentration of a nucleic acid denaturing agent to lower the $T_m$ of the hybrid formed from the first and second nucleic acid molecules.

22. The method of claim 21 wherein said concentration of nucleic acid denaturing agent ranges from about 5% by volume to about 95% by volume.

23. The method of claim 21 wherein said nucleic acid denaturing agent is alcohol ranging in concentration from about 10% by volume to 20% by volume and said strong nucleic acid precipitating agent is $(NH_4)_2SO_4$.

24. The method of claim 2 wherein the pH of said aqueous reaction solution ranges from about 4 to about 11.

25. The method of claim 2 wherein said temperature ranges from about room temperature to about 90° C.

26. A method for detecting the presence of a bacterium in a sample suspected of containing said bacterium, said method comprising:
preparing an aqueous reaction solution containing, in solution, a first quantity of a test sample suspected of containing said bacterium, said test sample having been treated with a quantity of a denaturing agent sufficient to disassociate the double-stranded nucleic acid molecules present in said bacterium into single-stranded nucleic acid molecules, a second quantity of a second single-stranded nucleic acid molecule complementary to the base sequence of a nucleic acid molecule of said bacterium to be detected so as to allow for the formation of a double-stranded molecule, and a concentration of at least one nucleic acid precipitating agent dissolved therein consisting essentially of an amount sufficient to precipitate said first and second single-stranded nucleic acid molecules so as to increase the rate of formation at least 100 times the formation rate for the same said double-stranded nucleic acid molecule in said reaction solution, comprising 0.18M NaCl in said reaction solution in place of said agent, at 60° C.;
incubating said aqueous reaction solution at a temperature at which reassociation can occur; and,
assaying said incubated aqueous reaction solution for the presence or amount of said double-stranded nucleic acid molecule.

27. The method of claim 26 wherein said nucleic acid precipitating agent is selected from the group consisting of detergent, dihydroxybenzene, sodium dodecyl sulfate, sodium diisobutyl sulfosuccinate, sodium tetradecyl sulfate, N-lauroylsarcosine sodium salt and the alkali metal salts and ammonium salts of $SO_4$, $PO_4$, Cl and HCOO.

28. The method of claim 26 wherein said concentration ranges from about the 1M to about 10M.

29. The method of claim 26 wherein the concentration of said denaturing agent ranges from about 5% by volume to about 95% by volume.

30. The method of claim 26 wherein the pH of said aqueous reaction solution ranges from about 4 to about 11.

31. The method of claim 26 wherein said temperature ranges from about room temperature to about 90° C.

32. The method of claim 26 wherein said nucleic acid precipitating agent is sodium phosphate.

33. The method of claim 26 wherein said nucleic acid precipitating agent is $NaSO_4$.

34. The method of claim 26 wherein said nucleic acid precipitating agent is LiCl.

35. The method of claim 26 wherein said nucleic acid precipitating agent is $(NH_4)_2SO_4$.

36. The method of claim 26 wherein said nucleic acid precipitating agent is 13 volume % 30 volume % N-lauroylsarcosine sodium salt.

37. The method of claim 26 wherein said nucleic acid precipitating agent is sodium dodecyl sulfate.

38. The method of claim 26 wherein said nucleic acid precipitating agent is sodium diisobutyl sulfosuccinate.

39. The method of claim 26 wherein said nucleic acid precipitating agent is sodium tetradecyl sulfate.

40. A method as defined in any one of claims 1, 2, 19, and 26 wherein the nucleic acid precipitating agent concentration is sufficient so as to increase the rate at least 1000 times the rate in 0.18M NaCl at 60° C.

41. The method of claim 1 or 2 further comprising the step of assaying said incubated aqueous reaction solution for the presence or amount of said double-stranded nucleic acid molecule.

42. A method as defined in claim 4 wherein the nucleic acid precipitating agent concentration is sufficient to increase the rate at least 1000 times the rate in 0.18M NaCl at 60° C.

43. A method as defined in claim 5 wherein the nucleic acid precipitating agent concentration is sufficient to increase the rate at least 1000 times the rate in 0.18M NaCl at 60° C.

44. A method as defined in claim 6 wherein the nucleic acid precipitating agent concentration is sufficient to increase the rate at least 1000 times the rate in 0.18M NaCl at 60° C.

* * * * *